("(12) United States Patent" / "Siess et al.")

United States Patent

(10) Patent No.: US 11,793,997 B2
(45) Date of Patent: Oct. 24, 2023

(54) PUMP, IN PARTICULAR A BLOOD PUMP

(71) Applicant: ECP ENTWICKLUNGSGESELLSCHAFT MBH, Aachen (DE)

(72) Inventors: Thorsten Siess, Aachen (DE); Mario Scheckel, Berlin (DE); Jörg Schumacher, Teltow (DE)

(73) Assignee: ECP ENTWICKLUNGSGESELLSCHAFT MBH, Aachen (DE)

( * ) Notice: Subject to any disclaimer, the term of this patent is extended or adjusted under 35 U.S.C. 154(b) by 895 days.

(21) Appl. No.: 15/766,882

(22) PCT Filed: Oct. 4, 2016

(86) PCT No.: PCT/EP2016/073702
§ 371 (c)(1),
(2) Date: Apr. 9, 2018

(87) PCT Pub. No.: WO2017/060257
PCT Pub. Date: Apr. 13, 2017

(65) Prior Publication Data
US 2018/0303990 A1    Oct. 25, 2018

(30) Foreign Application Priority Data
Oct. 9, 2015   (EP) .................................... 15189241

(51) Int. Cl.
*A61M 60/126*     (2021.01)
*A61M 60/857*     (2021.01)
(Continued)

(52) U.S. Cl.
CPC .......... *A61M 60/857* (2021.01); *A61M 60/13* (2021.01); *A61M 60/237* (2021.01);
(Continued)

(58) Field of Classification Search
CPC .... A61M 1/125; A61M 1/101; A61M 1/1034; A61M 1/122
See application file for complete search history.

(56) References Cited

U.S. PATENT DOCUMENTS 5,695,471 A * 12/1997 Wampler .............. F16C 39/063
                                                    604/131
6,533,716 B1 * 3/2003 Schmitz-Rode ...... F04D 29/242
                                                    600/16
(Continued)

FOREIGN PATENT DOCUMENTS

CN    101854964 A    10/2010
EP    2868331 A2    5/2015
(Continued)

OTHER PUBLICATIONS

PCT International Search Report for PCT/EP2016/073702, dated Dec. 12, 2016. (2 pages).
(Continued)

*Primary Examiner* — Michael J D'Abreu
(74) *Attorney, Agent, or Firm* — Botos Churchill IP Law LLP

(57) ABSTRACT

The application relates to a pump, in particular blood pump. The pump comprises a drive shaft (3) which runs in an axial direction, a delivery element (6) which is connected to the drive shaft (3) in a distal region of this, and a housing (5) which surrounds the delivery element (6). The delivery element (6) and the housing (5) are designed in a manner such that these automatically unfold after a forced compression. The housing (5) moreover comprises an inlet region (22) with at least one inlet opening (23), a fluid-tight region (20) which surrounds a region of the delivery element (6), and an outlet region (24) with at least one opening (23) for the exit of the pump medium. The delivery element (6) is
(Continued)

Figure 1:
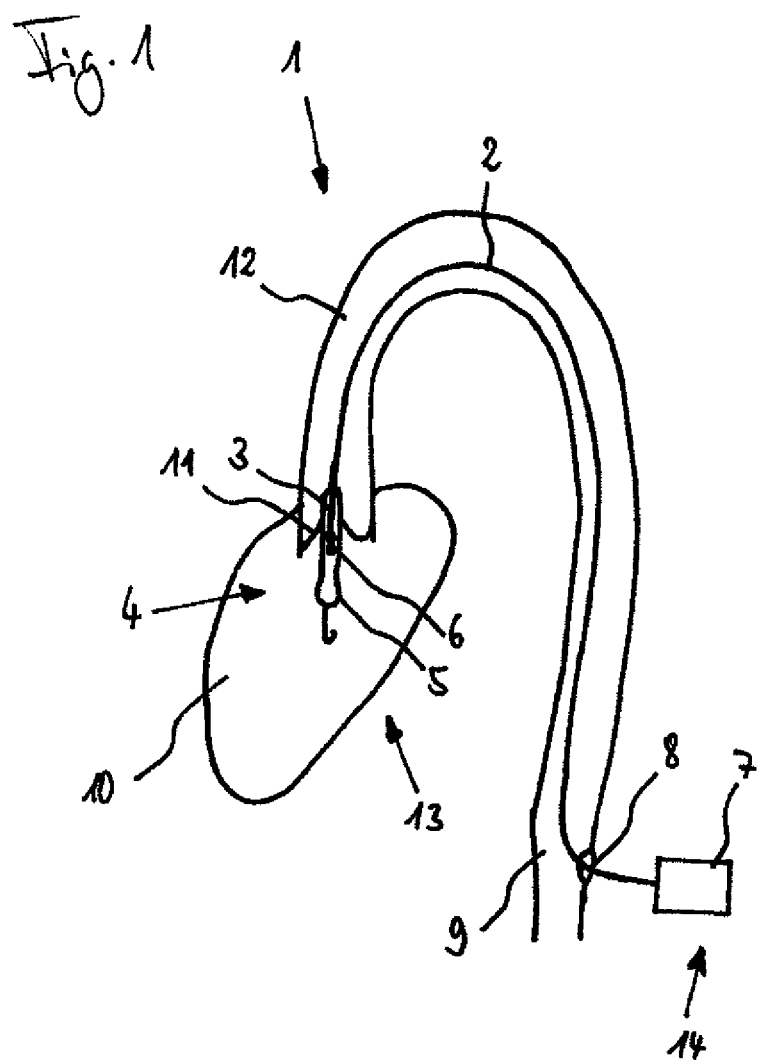

arranged in a manner such that it projects into the outlet region (24).

19 Claims, 5 Drawing Sheets

(51) Int. Cl.
| | |
|---|---|
| *A61M 60/894* | (2021.01) |
| *A61M 60/237* | (2021.01) |
| *A61M 60/13* | (2021.01) |
| *A61M 60/414* | (2021.01) |
| *A61M 60/825* | (2021.01) |
| *A61M 60/81* | (2021.01) |
| *A61M 60/808* | (2021.01) |

(52) U.S. Cl.
CPC ........ *A61M 60/414* (2021.01); *A61M 60/808* (2021.01); *A61M 60/81* (2021.01); *A61M 60/825* (2021.01); *A61M 60/894* (2021.01); *A61M 2205/0238* (2013.01); *A61M 2205/0266* (2013.01)

(56) References Cited

U.S. PATENT DOCUMENTS

| | | |
|---|---|---|
| 2004/0044266 A1 | 3/2004 | Siess et al. |
| 2008/0114339 A1 | 5/2008 | McBride et al. |
| 2009/0093764 A1* | 4/2009 | Pfeffer ................ A61M 1/1031 604/151 |
| 2011/0004046 A1 | 1/2011 | Campbell et al. |
| 2012/0178986 A1 | 7/2012 | Campbell et al. |
| 2014/0255176 A1* | 9/2014 | Bredenbreuker ..... F04D 29/247 415/208.1 |

FOREIGN PATENT DOCUMENTS

| | | |
|---|---|---|
| JP | H04156856 A | 5/1992 |
| JP | 2003504091 A | 2/2003 |
| JP | 2004514506 A | 5/2004 |
| JP | 2008519624 A | 6/2008 |
| JP | 2009530041 A | 8/2009 |
| JP | 2012531975 A | 12/2012 |
| WO | 2006051023 A1 | 5/2006 |
| WO | 2009/046789 | 4/2009 |

OTHER PUBLICATIONS

Office Action corresponding to Chinese Patent Appl. No. 201680059008.2 dated Mar. 24, 2020 (15 pages).
Reasons for Refusal issued in corresponding Japanese Patent Application No. 2018-517851 dated Aug. 25, 2020 (10 pages).
Office Action issued in Canadian Patent Application No. 3,000,581, dated Jan. 20, 2023 (6 pp.).
Office Action in Japanese Patent Application No. 2021-023196, dated Apr. 5, 2022, (6 pp).
Office Action from corresponding Korean Application No. 10-2018-7011270 dated Apr. 12, 2023 (21 pages).

* cited by examiner

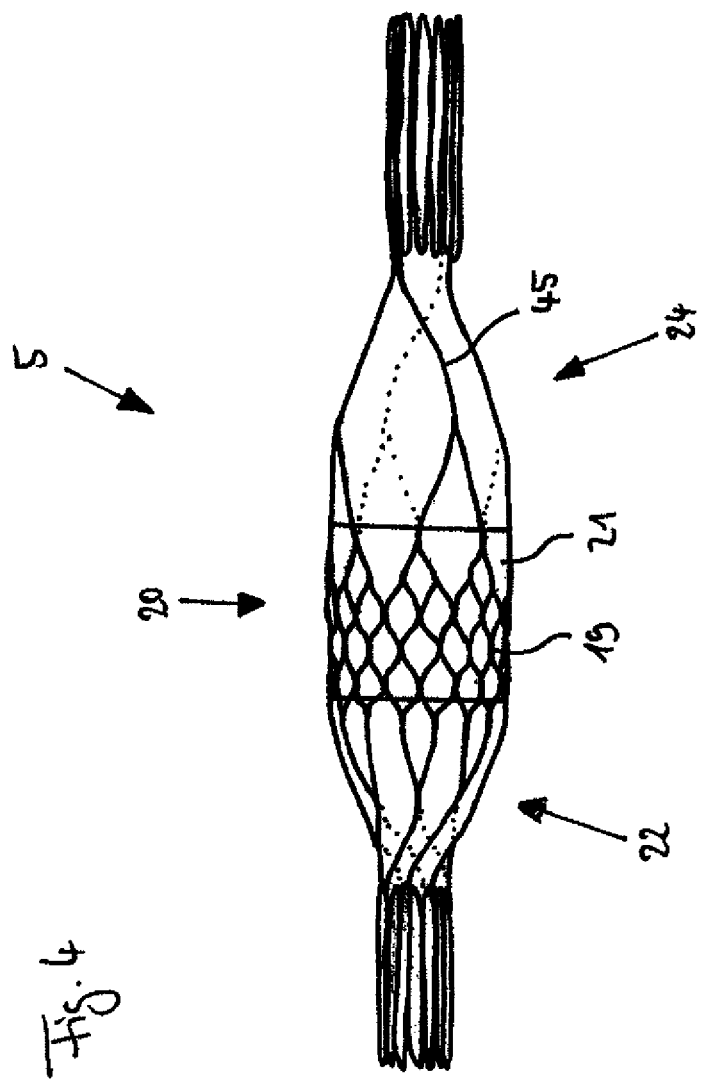

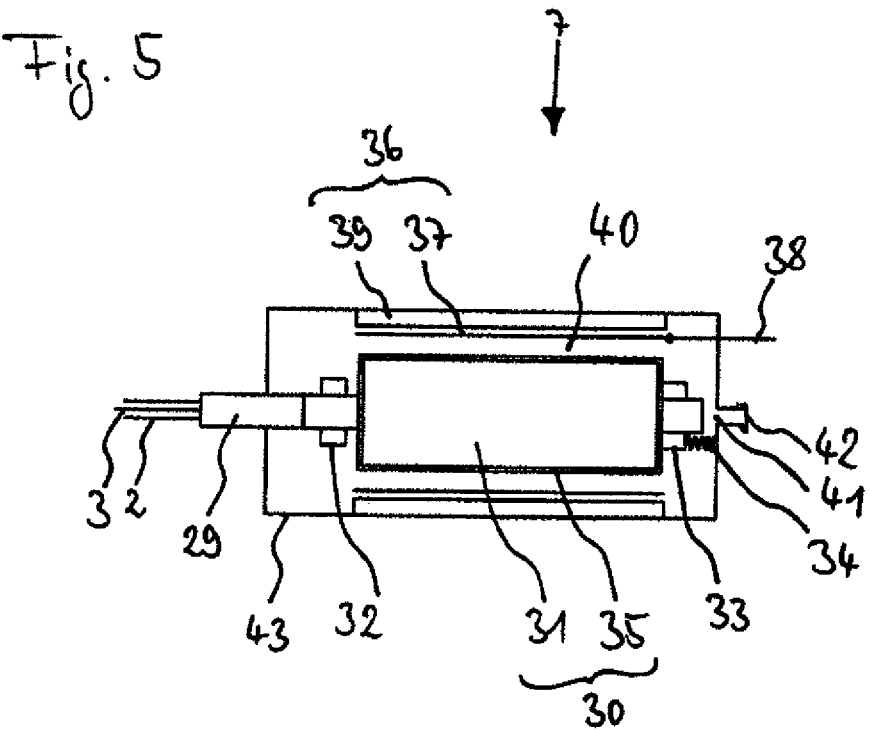
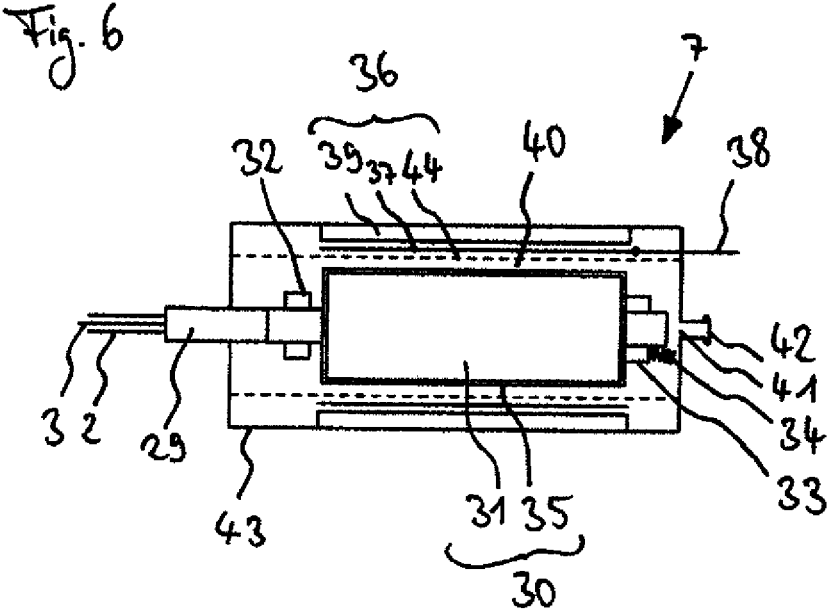

PUMP, IN PARTICULAR A BLOOD PUMP

CROSS-REFERENCE TO RELATED APPLICATIONS

This application is a United States National Stage filing under 35 U.S.C. § 371 of International Application No. PCT/EP2016/073702, filed Oct. 4, 2016, which claims the benefit of European Patent Application No. 15189241.1, filed Oct. 9, 2015, the contents of all of which are incorporated by reference herein in their entirety. International Application No. PCT/EP2016/073702 was published under PCT Article 21(2) in English.

The application relates to a pump, in particular to a blood pump, according to the preamble of claim 1.

Blood pumps with a proximal and a distal end as well as with a catheter which is arranged therebetween, and in which pumps a flexible drive shaft is guided in an interior of the catheter, are known from the state of the art. Such blood pumps at their distal end typically comprise a pump head which comprises a foldable housing and a foldable delivery element, wherein the delivery element is connected to a distal region of the drive shaft. Such pump heads can be led to locations which are difficult to access. For example, such a pump head can be inserted through the femoral artery, via the aortic arch, into a region of the aortic valve of a patient, in order there to deliver blood from the left ventricle of the heart into the aorta. The drive shaft is driven at the proximal end of the blood pump by way of a motor which is typically located outside the body of the patient. Such a blood pump is described for example in the document EP 2 868 331 A2.

It is the object of the invention to suggest an improved pump, in particular an improved blood pump, which is more efficient in operation.

This object is achieved by a pump with the features of the main claim. Advantageous further developments are derivable from the features of the dependent claims and of the embodiment examples.

The suggested pump, in particular blood pump, comprises a drive shaft which runs in an axial direction, a delivery element which is connected to the drive shaft in the distal region of this, and a housing which surrounds the delivery element. The delivery element and the housing are designed in a manner such that these automatically unfold after a forced compression. The housing moreover comprises an inlet region with at least one inlet opening, a fluid-tight region which surrounds a region of the delivery element, and an outlet region with at least one opening for the exit of a pump medium. The delivery element is arranged in a manner such that it projects into the outlet region.

In particular, one can envisage the delivery element being arranged in a manner in which it projects into the outlet region in an expanded condition of the housing and of the delivery element. The outlet region surrounds a region of the delivery element which is arranged in the delivery direction. Due to the at least one opening of the outlet region, the delivery element is not completely enclosed in a fluid-tight manner in the outlet region. The outlet region can hence surround a region of the delivery element which is situated at an end of the delivery element which points in the delivery direction. The fluid-tight region typically connects to an end of the inlet region which is situated in the delivery direction, and the outlet region typically connects to an end of the fluid-tight region which is situated in the delivery direction. The inlet region, the fluid-tight region and the outlet region, at least in some portions, typically have an essentially annulus-shaped cross section. One envisages the pump medium flowing through the inlet region into the housing and leaving the housing via the outlet region on operation of the pump.

Typically in the outlet region, the housing comprises lateral openings additionally to the axial openings, so that a delivered pump medium, in the outlet region, can flow out of the housing in the radial direction, or perpendicularly to the drive shaft axis, or has at least a radial speed component when flowing out.

Surprisingly, it has been found that the pump output can be drastically increased by way of such an arrangement, compared to known blood pumps of the type described above. Given an equal motor power for example, a fluid volume which is delivered in a given time interval can be increased by up to 50% in this manner.

Typically, the delivery element here projects partly out of the fluid-tight region. The delivery element then projects partly into the outlet region.

For example, one can envisage the outlet region overlapping an axial extension of the delivery element by at least 5%, preferably by at least 10%, particularly preferably by at least 25%.

Moreover, one can envisage the outlet region overlapping an axial extension of the delivery element by 75% at the most, preferably by 65% at the most, particularly preferably by 50% at the most.

The housing typically comprises a lattice, in particular in the outlet region. The lattice can comprise a shape memory material or a suitable memory alloy, so that the lattice can be reliably expanded and compressed. The lattice can comprise for example nitinol, a plastic, an iron alloy or a copper alloy. One can envisage the housing comprising a lattice in the inlet region and/or in the fluid-tight region and/or in the outlet region.

Typically, the housing comprises an elastic covering. The elastic covering can be arranged for example on an inner side and/or an outer side of a possibly present lattice. A covering is suitable for closing lattice openings, and may be, for example, a polyurethane covering. However, for example polyethylene, polypropylene, silicone or parylenes can also be used.

The fluid-tight region can be formed at least partly by way of the elastic covering. The outlet region and the inlet region are typically formed by the lattice with its lattice openings, whereas the fluid tight region between the outlet region and the inlet region is formed by a covering of the lattice by the elastic covering.

In the expanded condition, one can envisage the housing having a conical section tapering conically in the delivery direction, in the outlet region. In its expanded condition, one can also envisage the housing having a conical section widening in the delivery direction, in the inlet region.

In an expanded condition, the housing can moreover comprise an essentially tubular section in the outlet region, said section being connected to the conical section at an end which is situated in the delivery direction. The tubular section of the outlet region can merge into a tubular section of the fluid-tight region at an end which is opposite to the delivery direction.

Typically, the lattice has larger lattice openings in the outlet region than in the fluid-tight region. Moreover, one can envisage the lattice comprising larger lattice openings in the inlet region than in the fluid-tight region. Damage to the blood due to the pump can be prevented or at least minimised by way of an enlargement of the openings in the regions of the housing which are subjected to through-flow.

One can envisage a region of the outlet region being surrounded by an outflow element. In particular, one can envisage a region of the outlet region being surrounded by an outflow shield which extends from the pump housing in the delivery direction. This outflow shield can essentially have a shape which corresponds to a lateral surface of a truncated cone. Typically, a tapered end of the outflow shield is fastened to the housing, in particular in the fluid-tight region. A widening end of the outflow shield can be aligned in the delivery direction, so that the outflow shield partly or completely encloses the outlet region. The flow conditions in the pump can be further optimised by the outflow shield, by which means the delivery output can be improved.

It is also possible for a region of the outlet region to be surrounded by an outflow tube which extends from the pump housing in the delivery direction. Typically, the outflow tube is designed in such a flexible manner that it forms a check valve. Such an outflow tube, similarly to the outflow shield, can contribute to a further optimisation of the flow conditions and to an improvement of the pump output. For example, an outflow tube as is described in the document EP 2 345 440 B1 is possible.

Typically, the inlet region does not overlap with an axial extension of the delivery element. The delivery element can therefore be arranged in a manner such that this does not project into the inlet region. A shielding of the delivery element from parts of the body of a patient can be achieved in a suction region of the pump by way of this, by which means an injury to the patient can be avoided.

The drive shaft is typically connected to a motor for driving the drive shaft, at a proximal end of the drive shaft. The shaft can be for example a flexible shaft which is guided in a catheter.

The pump can be configured for pumping blood from a ventricle into a blood vessel of a patient, wherein the drive shaft, in a proximal region, is configured for connection to a motor which is outside a body of a patient. The motor can be designed for example for fastening to a thigh of a patient. The catheter and the drive shaft can have an adequate length of at least 50 cm, preferably at least 90 cm for this purpose. A maximal length of the flexible drive shaft can be 200 cm, preferably 150 cm.

The lattice can be designed as a rhomboid lattice with essentially rhomboidal lattice openings, in a region of the housing.

One can envisage the lattice comprising lattice struts, wherein a number of the lattice struts along a periphery of the rhomboid lattice is $m \cdot 2^n$, with m and n being natural numbers, preferably 32 or 40, wherein m is greater than 2, preferably greater than 3. One can also envisage the housing, in the outlet region, comprising m, preferably 4 or 5 lattice struts along a periphery.

Such a design permits a particularly stable reduction of the lattice struts, for example in the direction of a distal end or in the direction of a proximal end of the housing. Furthermore, a particularly stable enlargement of the lattice openings can be achieved in this manner. Here, one can envisage all lattice struts being merged in pairs in the shape of a Y along a periphery of the housing at a certain axial position. Such a merging can be effected repeatedly at one or more further axial positions of the housing. Given a presence of, for example, 5 struts and openings along the periphery of the housing, a stepwise increase in the number of struts to 10, 20, 40, . . . can be therefore, for example, be effected at an end of the housing. Having begun, for example, with 4 (3) struts and openings along the periphery of the housing, the number of struts and openings can also be increased in steps to 8 (6), 16 (12), 32 (24), . . . . Here, n indicates a number of the steps and m a number of struts and openings along a periphery of the housing at an axial position, at which the merging begins.

The application moreover relates to a blood pump which comprises a drive shaft running in an axial direction, a delivery element which is connected to the drive shaft in a distal region of this, and a housing which surrounds the delivery element. The delivery element and the housing are designed in a manner such that these automatically unfold after a forced compression. The housing comprises a lattice, an inlet region with at least one inlet opening, a fluid-tight region, which surrounds a region of the delivery element, and an outlet region with at least one opening for the exit of a pump medium. The lattice moreover comprises lattice openings and lattice struts, wherein a number of the lattice struts along a periphery of the lattice at a first axial position of the lattice is m and wherein the lattice is designed in a manner such that the number of lattice struts along a periphery of the lattice increases in an axial direction with n steps to $m \cdot 2^n$ lattice struts at a second axial position of the lattice, wherein m and n are natural numbers and m is larger than 2, preferably larger than 3. m can be for example 3, 4 or 5. Alternatively m can be for example 6, 8 or 10.

Typically, one envisages the number of lattice struts along the periphery of the lattice at the second axial position of the lattice being 32 or 40. Moreover, one typically envisages the housing comprising m, preferably 4 or 5 lattice struts along a periphery in the outlet region. Injury to the blood when it flows through the lattice struts of the outlet region can be reduced by way of such an embodiment.

Figure 2:
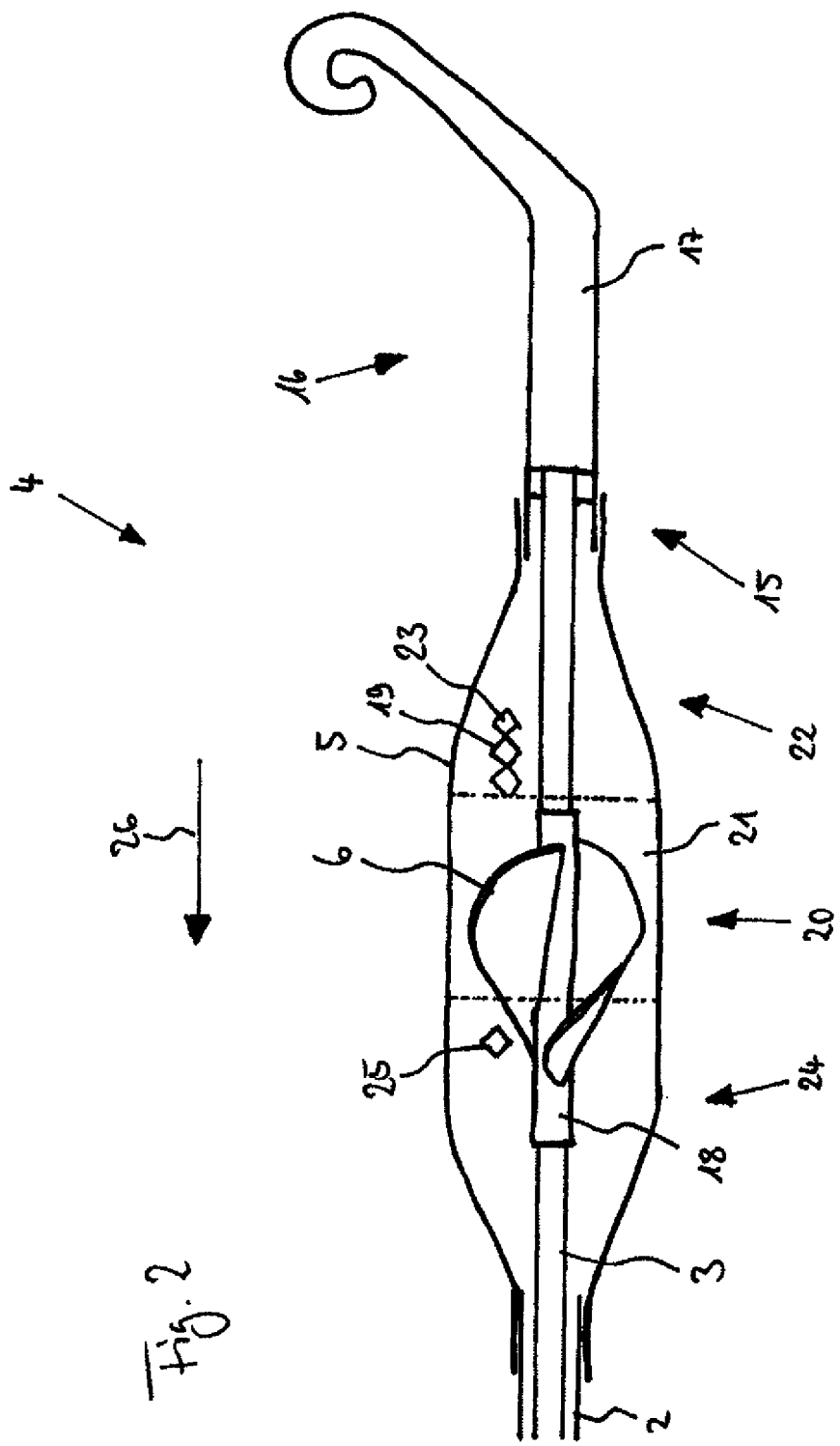
Figure 3A:
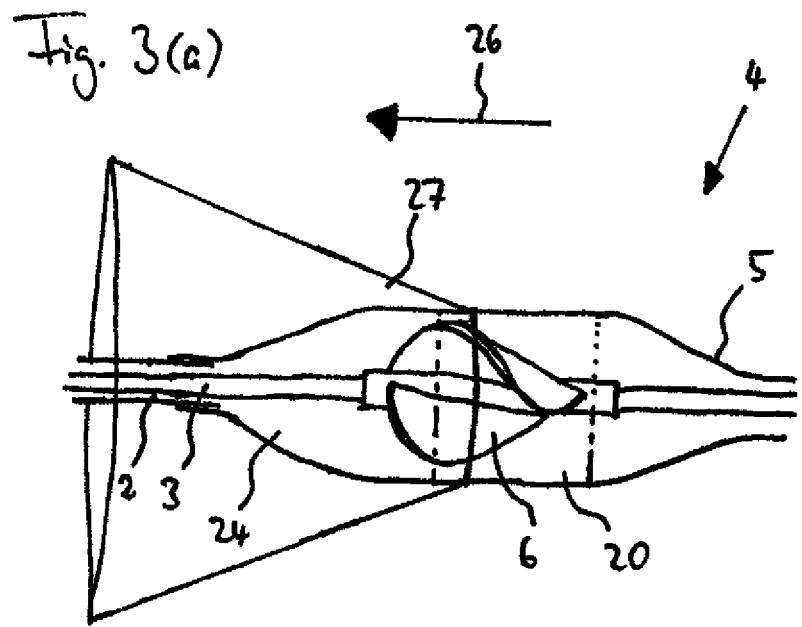
Figure 3B:
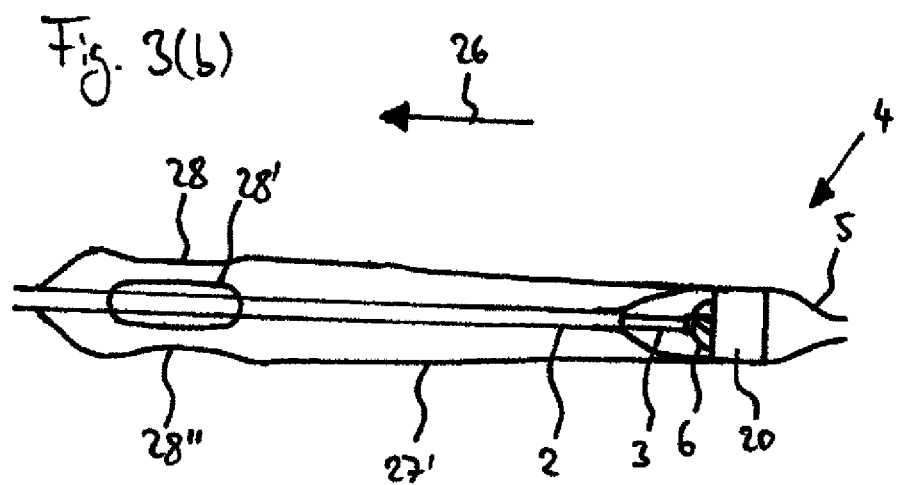

Embodiment examples of the invention are hereinafter described by way of the drawings. There are shown in:

FIG. 1 a schematic representation of a pump arrangement,

FIG. 2 a schematic representation of a pump head,

FIGS. 3(*a*), (*b*) two further schematic representations of the pump head,

FIG. 4 a schematic representation of a housing,

FIG. 5 a schematic representation of a motor and

FIG. 6 a schematic representation of a further motor.

FIG. 1 schematically shows a pump arrangement 1. The pump arrangement 1 comprises a catheter 2, in which a flexible drive shaft 3 is guided. The catheter 2 is connected to a pump head 4. This pump head 4 comprises a housing 5 and a delivery element 6 which is arranged in the housing 5 and which can be driven via the drive shaft 3 by a motor 7 connected to the proximal end of the drive shaft 3. The pump head 4 as well as the catheter 2 and the drive shaft 3 are introduced into the femoral artery 9 via a port 8, in a manner such that the pump head 4 in the region of the left ventricle 10 is located in the region of the aortic valve 11. On operation, the drive shaft 3 is driven by the motor 7 and the pump arrangement 1 delivers blood from the left ventricle 10 into the aorta 12. In the shown arrangement for left heart assistance, a delivery direction of the pump arrangement 1 corresponds to the direction from a distal end 13 of the pump arrangement 1 to a proximal end 14 of the pump arrangement 1.

However, the pump arrangement 1 can also be configured for a delivery of blood in a direction from the proximal end 14 to the distal end 13 of the pump arrangement 1, which is suitable for example for right heart assistance.

The pump head 4 is represented schematically in FIG. 2. Recurring features in this and in the subsequent drawings are provided with the same reference numerals. The pump head 4 comprises the delivery element 6 and the housing 5. The delivery element 6 in the present example is designed as a pump rotor with two flexible segments in the form of rotor blades. Additionally, the drive shaft 3, which is mounted on a distal region 15 of the pump head 4, is represented. A so-called pigtail 17, which is manufactured from an elastically deformable material, is provided at the distal end 16 of the pump head 4. A cylindrical element 18 is rigidly connected to the drive shaft 3. The delivery element 6 is fastened to the cylindrical element 18. The delivery element 6 as well as the housing 5 are designed in such an unfoldable manner that they can automatically unfold after a forced compression. The delivery element 6 is manufactured from a plastic. The housing 5 is manufactured from the shape memory material nitinol. The complete pump head 4 can be unfolded due to the fact that the delivery element 6 as well as the housing 5 are designed in an unfoldable manner.

The housing 5 is designed as a rhomboidal lattice 19 and in a fluid-tight region 20 comprises an elastic covering 21 of polyurethane. The elastic covering 21 covers an inner side and an outer side of the rhomboidal lattice 19 in a manner such that rhomboid lattice openings which are formed by the lattice 19 in the fluid-tight region 20 can be closed in a fluid-tight manner by way of the elastic covering 21.

The housing 5 moreover comprises an inlet region 22 which is not covered by the elastic covering 21. In the inlet region 22, the rhomboid lattice openings form inlet openings, of which one is provided, by way of example, with the reference numeral 23 in FIG. 2. The housing 5 moreover comprises an outlet region 24 which is likewise not covered by the elastic covering 21. In the outlet region 24, the rhomboid-like lattice openings form outlet openings, of which one is represented by way of example and is provided with the reference numeral 25.

On operation of the pump arrangement 1, the drive shaft 3 is driven by the motor 7, so that the delivery element 6, which is connected to the drive shaft 3, rotates about an axis of the drive shaft 3. By way of this, blood is transported through the inlet openings of the inlet region 22 into the housing 5 and subsequently exits through the outlet openings of the outlet region 24, out of the housing 5. Blood is delivered in a delivery direction 26 by way of the pump arrangement 1 in this manner.

The elastic covering 21 does not completely surround the axial extension of the delivery element 6. Instead, the delivery element 6 projects partly into the outlet region 24, so that at least the outlet opening with the reference numeral 25 is arranged laterally, i.e. in the radial direction, next to the delivery element 6. In contrast, the elastic covering 21 at its distal end is designed in a manner such that the delivery element 6 does not project or does not significantly project into the inlet region 22 and is therefore not laterally surrounded by inlet openings.

The design of the elastic covering 21 and the delivery element 6 and their arrangement with respect to one another is such that roughly a third of the axial extension of the delivery element 6 is not surrounded by the elastic covering 21 which forms the fluid-tight region 20. In the shown example, the same share of the axial extension of the delivery element 6 is surrounded by the outlet region 24.

The pump head 4 additionally comprises an outflow element. This can be designed as an outflow shield 27 as is represented in FIG. 3(*a*), or as an outflow tube 27' as is represented in FIG. 3(*b*).

The outflow shield 27, which is represented in FIG. 3(*a*), is fastened to the housing 5 in the fluid-tight region 20 of the housing 5. The outflow shield 27 has the shape of a lateral surface of a truncated cone and extends in the delivery direction 26 such that this shield is widened in the delivery direction 26. The delivery element 6 and the outlet region 24 are surrounded by the outflow shield 27. In another embodiment, one can also envisage the outlet region 24 being partly surrounded by the outflow shield 27

The pump head 4 in FIG. 3(*b*) only differs from the pump head 4 represented in FIG. 3(*a*) in that an outflow tube 27' is provided instead of the outflow shield 27. This outflow tube 27 is fastened to the housing 5 in the fluid-tight region 20 and extends from there in the delivery direction 26. The outflow tube 27' is manufactured from polyurethane and comprises openings 28, 28', 28" in a region situated in the delivery direction 26. In the example shown, the outlet region 24 is completely surrounded by the outflow tube 27'. The outflow tube 27' is flexible and closes automatically when a blood flow occurs in a direction that is opposite to the delivery direction 26, due to the outflow tube 27' being pressed onto the catheter 2 and/or onto the housing 5.

FIG. 4 schematically shows the rhomboidal lattice 19 of the housing 5. The fluid-tight region 20 with the elastic covering 21 as well as the inlet region 22 and the outlet region 24 are additionally represented. Regions of the inlet region 22 and of the outlet region 24 have a conical shape, whereas the fluid-tight region 20 is essentially tubular. The lattice 19 comprises lattice struts, of which one is characterised by way of example by the reference numeral 45. The lattice struts 45 run in a manner such that the essentially rhomboidal lattice openings are larger in the inlet region 22 as well as in the outlet region 24 than in the fluid-tight region 20. Lattice struts which are arranged on a side of the housing 5 which is away from the viewer are merely represented in FIG. 4 in a dotted manner for an improved overview.

In the fluid-tight region 20, the lattice struts 45 form a comparatively finely meshed lattice. The lattice 19, along a peripheral of the housing 5 in the fluid-tight region 20, comprises thirty-two struts or, inasmuch as the periphery is considered at an axial position of the housing 5 with node points, comprises sixteen nodes. A largely round cross section of the housing 5 in the fluid-tight region 20 is achieved by way of such a close-meshed lattice 19.

The number of lattice struts 45 along a periphery of the housing 5 is halved from the fluid-tight region 20 in the direction of the inlet region 22 and in the direction of the outlet region 24 by way of merging the lattice struts into pairs, so that the housing 5 in the corresponding regions comprises sixteen lattice struts 45 along the periphery, in which no node points are present. The number of lattice struts 45 is subsequently reduced once again in the direction of the inlet region 22 and of the outlet region 24, by way of merging the lattice struts into pairs, so that the housing 5 in these regions comprises eight lattice struts 45. A further reduction of the number of lattice struts 15 is effected in the outlet region 24 in the manner mentioned above, so that the housing 5 in a region situated further in the delivery direction 26 has only four lattice struts 45 along a periphery.

A lattice 19 with larger lattice openings than in the fluid-tight region 20 forms in the inlet region 22 and in the outlet region 24 on account of the described reduction of the number of lattice struts 45.

The lattice struts 45 in the conical regions of the outlet region 24 and of the inlet region 22 form a spiral-shaped structure, which leads to a reliable unfolding of the pump head 4 when pushing the pump head 4 out of a cannula.

FIG. 5 shows a schematic view of the motor 7. The motor 7, in the region of a shaft stub 29, is connected to the catheter 2, which is glued into the shaft stub 29. The flexible drive shaft 3 is guided in the catheter 2. The motor 7 moreover comprises a rotor 30, which has a rotor magnet 31.

The flexible drive shaft 3 is connected to the rotor 30 in a manner such that given a rotation of the rotor 30, a torque is transmitted from the rotor 30 to the flexible drive shaft 3. The torque is transmitted to the delivery element 6 via the flexible drive shaft, so that the pump arrangement is driven by the motor 7.

The rotor 30 is axially mounted by way of two bearings 32, 33. One of these bearings 33 is biased by way of a spring element 34 for an axial stabilisation of the rotor 30. The spring element 34 can be designed, for example, as a helical spring or as an annular spring. The bearings 32, 33 can each be designed as ball bearings or as plain bearings. If the bearings 32, 33 are designed as ball bearings, then the bearings 32, 33 comprise balls of ceramic and cages of plastic so that the ball bearings have non-magnetisable material. The rings of the bearings can be designed for example from a magnetisable metal or from a non-magnetisable material. If the bearings 32, 33 are designed as plain bearings, then they each comprise friction partners of DLC-coated implant steel and yttrium-stabilised zirconium oxide.

The rotor magnet 31 comprises a biocompatible DLC coating. The motor 7 moreover comprises a stator 36. The stator 36 comprises several windings 37 which are connected in an electrically conductive manner to electricity connections 38. The stator 36 moreover comprises back iron laminations 39. The windings 37 are potted with a biocompatible epoxy resin which contains thermally conductive aluminum oxide.

A gap 40 with an annular cross section is formed between an inner side of the coating of the windings 37 and an outer side of the coating 35 of the rotor magnet 31. The gap 40 has a width of 0.2 mm. This gap 40 is in fluid connection with a rinsing opening 41, which is connected to a rinsing connection 42, wherein the rinsing connection 42 is arranged at a proximal end of the motor 7. The gap 40 is moreover in fluid connection with an intermediate space formed between the drive shaft 3 and the catheter 2. Thus, for example, a glucose solution can be rinsed through the rinsing opening 41 and the gap 40 and the intermediate space via the rinsing connection 42. Glucose solution rinses around the rotor 30 during operation in this manner. A radial distance between the outer side of the rotor magnet 31 and an inner side of the windings 37 is 0.5 mm. An inner radius of the windings 37 here corresponds to 1.1 times an outer radius of the rotor magnet 31.

The stator 36 and the rotor 30 are connected to one another in a manner that cannot be released by the user and are incorporated into a motor housing 43. The motor housing 43 can be connected, for example, to a grip or to a cooling body. The motor can be operated in a very efficient manner due to the small distance between the windings 37 and the rotor magnet 31, so that the motor housing 43 as well as a grip or cooling body, which may be connected to this housing, is heated to less than 40° C. at its exposed surfaces when the pump arrangement 1 is operated at a speed of 32,000 r.p.m and at a delivery output of 2.5 l per minute.

The motor 7' which is represented in FIG. 6 differs from the motor 7 represented in FIG. 6 merely in that the stator 36 in this embodiment comprises a fluid-tight sleeve 44 which delimits the gap 40. In this embodiment, the width of the gap 40 is 0.15 mm. The sleeve 44 comprises polyether ether ketone and is magnetically inactive. The sleeve 44 is arranged in a manner such that for example the windings 37 and further parts of the stator 36 are separated from the rinsing fluid which possibly flows through the gap 40, by way of the sleeve 44. An extension of the sleeve 44 in the axial direction is about 1.2 times an axial extension of the rotor magnet 31.

Features of the different embodiments which are merely disclosed in the embodiment examples can be combined with one another and claimed individually.

The invention claimed is:

1. A blood pump, comprising:
a drive shaft which runs in an axial direction;
a delivery element which is connected to the drive shaft in a distal region of the drive shaft; and
a housing which surrounds the delivery element, wherein the delivery element and the housing are configured to automatically unfold after a forced compression, wherein the housing comprises:
an inlet region with at least one inlet opening;
a fluid-tight region which surrounds a region of the delivery element, wherein the housing comprises an elastic covering and the fluid-tight region is formed at least partly by the elastic covering; and
an outlet region with at least one opening for exit of a pump medium, wherein the delivery element comprises a rotor and the rotor is configured such that it extends into the outlet region.

2. The blood pump according to claim 1, wherein the housing comprises a lattice.

3. The blood pump according to claim 2, wherein the lattice is configured as a rhomboid lattice with rhomboidal lattice openings, in a region of the housing.

4. The blood pump according to claim 3, wherein the lattice comprises lattice struts, wherein a number of lattice struts along a periphery of the rhomboid lattice is $m \cdot 2^n$, with m and n being natural numbers, wherein m is larger than 2.

5. The blood pump according to claim 4, wherein the housing has m lattice struts along a periphery in the outlet region.

6. The blood pump according to claim 2, wherein the lattice comprises a shape memory material.

7. The blood pump according to claim 2, wherein the lattice has larger lattice openings in the outlet region than in the fluid-tight region.

8. The blood pump according to claim 1, wherein the outlet region of the housing comprises a conical section tapering in a delivery direction when the housing is in an expanded condition.

9. The blood pump according to claim 8, wherein the outlet region of the housing comprises a tubular section which is connected to the conical section at an end which is situated in the delivery direction when the housing is in an expanded condition.

10. The blood pump according to claim 1, wherein a region of the outlet region is surrounded by an outflow tube which extends from the housing in a delivery direction.

11. The blood pump according to claim 10, wherein the outflow tube is configured to form a check valve.

12. The blood pump according to claim 1, wherein the outlet region overlaps an axial extension of the delivery element by at least 5%.

13. The blood pump according to claim 12, wherein the outlet region overlaps the axial extension of the delivery element by 75% at most.

14. The blood pump according to claim 1, wherein a region of the outlet region is surrounded by an outflow shield which extends from the housing in a delivery direction.

15. The blood pump according to claim 12, wherein the inlet region does not overlap with the axial extension of the delivery element.

16. The blood pump according to claim 1, wherein the drive shaft is connected to a motor at a proximal end of the drive shaft, the motor configured to drive the drive shaft.

17. The blood pump according to claim 1, wherein the drive shaft is a flexible shaft.

18. The blood pump according to claim 1, wherein the drive shaft is guided in a catheter.

19. The blood pump according to claim 1, wherein the blood pump is configured to pump blood from a ventricle into a blood vessel of a patient, wherein the drive shaft in a proximal region is configured for connection to a motor outside a body of the patient.

* * * * *